(12) United States Patent
Kitahara et al.

(10) Patent No.: US 7,585,930 B2
(45) Date of Patent: Sep. 8, 2009

(54) METHOD OF DECOMPOSING A POLYCARBONATE

(75) Inventors: Mai Kitahara, Iwakuni (JP); Masumi Hirata, Iwakuni (JP); Tetsuo Ban, Iwakuni (JP); Toru Sawaki, Iwakuni (JP)

(73) Assignee: Teijin Limited, Osaka (JP)

( * ) Notice: Subject to any disclaimer, the term of this patent is extended or adjusted under 35 U.S.C. 154(b) by 191 days.

(21) Appl. No.: 10/588,901

(22) PCT Filed: Feb. 8, 2005

(86) PCT No.: PCT/JP2005/002184

§ 371 (c)(1),
(2), (4) Date: Aug. 9, 2006

(87) PCT Pub. No.: WO2005/077515

PCT Pub. Date: Aug. 25, 2005

(65) Prior Publication Data

US 2007/0185309 A1    Aug. 9, 2007

(30) Foreign Application Priority Data

Feb. 12, 2004  (JP) ............................ 2004-034596
Mar. 29, 2004  (JP) ............................ 2004-094672

(51) Int. Cl.
*C08G 63/02* (2006.01)
*C08G 63/00* (2006.01)

(52) U.S. Cl. .................. 528/196; 428/412; 524/404; 524/495; 524/496; 562/483; 564/414

(58) Field of Classification Search .................. 428/412; 524/404, 495, 496; 562/483; 564/414
See application file for complete search history.

(56) References Cited

U.S. PATENT DOCUMENTS

| | | | |
|---|---|---|---|
| 6,255,529 B1 * | 7/2001 | Nagase et al. ................ 564/414 |
| 6,331,320 B1 * | 12/2001 | Nakahara et al. ............ 424/725 |
| 6,462,230 B1 | 10/2002 | Nagase et al. | |
| 2004/0054238 A1 * | 3/2004 | Ban et al. .................... 568/723 |

FOREIGN PATENT DOCUMENTS

| | | |
|---|---|---|
| CN | 1188776 A | 7/1998 |
| JP | 6-25086 B2 | 4/1994 |
| JP | 11-286572 A | 10/1999 |
| JP | 2000-53800 A | 2/2000 |
| JP | 2001-302844 A | 10/2001 |
| JP | 2003-41049 A | 2/2003 |

OTHER PUBLICATIONS

Organic Chemical Reactions in Supercritical Water; by Phillip E. Savage, Chem. Rev., 99 (2), 603-622, 1999.*

* cited by examiner

*Primary Examiner*—Terressa M Boykin
(74) *Attorney, Agent, or Firm*—Sughrue Mion, PLLC

(57) ABSTRACT

A method of decomposing a polycarbonate with water in a supercritical or subcritical state. A high-purity dihydroxy compound which is a constituent component of the polycarbonate can be recovered at a high yield by this decomposition method. This decomposition method is environment-friendly because it does not use an organic solvent, easy to be carried out, has a high decomposition rate and rarely causes a side reaction.

4 Claims, No Drawings

METHOD OF DECOMPOSING A POLYCARBONATE

FIELD OF THE INVENTION

The present invention relates to a method of decomposing a polycarbonate with water in a supercritical or subcritical state. More specifically, it relates to a method of recovering a dihydroxy compound as a raw material by decomposing a polycarbonate in accordance with the above method.

DESCRIPTION OF THE PRIOR ART

Polycarbonate resins have excellent heat resistance, impact resistance and transparency and are mass-produced and consumed in large quantities for use as optical materials for lenses and compact disks and further in a wide variety of fields such as construction materials, auto parts and OA equipment. The consumption of the resins has been increasing every year and is expected to further grow in the future.

There are also known polycarbonate compound resins prepared by blending an olefin-based resin such as acrylonitrile-butadiene-styrene (ABS) resin with a polycarbonate resin. Since the polycarbonate compound resins have excellent impact resistance, fluidity, toughness and flame retardancy and their molded products are rarely warp, they are widely used in a wide variety of fields such as home electric appliances, OA equipment, electronic and electric parts and daily goods.

After the above polycarbonate resins and polycarbonate compound resins are put on the market and their service lives pass, they are exchanged for new products and generally scrapped. The total amount of these waste plastics has been increasing every year and about 60% of the total amount is disposed of by simple burning and burying in the ground. However, carbonic acid gas is discharged into the air by simple burning, thereby causing a problem from the viewpoint of global warming. Meanwhile, when it is buried in the ground, waste plastics are light and bulky and therefore occupy a large volume. Therefore, in the current situation where a shortage of land for final waste disposal facilities such as reclaimed land is an urgent problem to be solved, it is impossible to continue this disposal method in the future. Consequently, it is extremely important from the viewpoints of waste disposal and earth resources, that is, the prevention of the exhaustion of oil resources that the above polycarbonate resins and polycarbonate compound resins be collected from the market and recycled.

The methods of recycling waste plastics are roughly divided into (1) a material recycling method in which waste plastics are re-used as they are, (2) a chemical recycling method in which waste plastics are depolymerized into monomers or chemically decomposed to recover useful chemical raw materials and (3) a thermal recycling method in which waste plastics are recovered as thermal energy. Since the chemical recycling method out of these recycling methods recovers chemical raw materials, synthetic resins and chemical products can be newly synthesized from waste plastics and can be used in a wide variety of fields.

To decompose a polycarbonate resin for chemical recycling, JP-A 2003-41049 (the term "JP-A" as used herein means an "unexamined published Japanese patent application") discloses a method of obtaining a dihydroxy compound and dimethyl carbonate by carrying out ester interchange using methanol in a supercritical state as a solvent. JP-B 6-25086 (the term "JP-B" as used herein means an "examined Japanese patent publication") proposes a method of obtaining a dihydroxy compound by hydrolyzing a polycarbonate resin in the presence of an ammonia aqueous solution.

As for the recycling of a polycarbonate compound resin JP-A 2001-302844 reports a method of recovering bisphenol A and urea as useful chemical raw materials from a decomposed product obtained by chemically decomposing a polycarbonate resin contained in a waste plastic in a solution containing a halogen-based organic solvent which dissolves both polycarbonate resin and ABS resin contained in a PC/ABS resin alloy and an ammonia aqueous solution. However, since the above method uses a large amount of the halogen-based organic solvent, its bad influence upon environment is apprehended and a post-treatment such as the neutralization of the ammonia aqueous solution is complicated and greatly impairs economic efficiency. Therefore, the above method is not suitable for the disposal and recycling of a large amount of the polycarbonate compound resin.

SUMMARY OF THE INVENTION

It is an object of the present invention to provide a method of decomposing a polycarbonate without using an organic solvent.

It is another object of the present invention to provide a method of decomposing a polycarbonate at a high rate by suppressing a side reaction.

It is still another object of the present invention to provide an industrially simple and advantageous method of decomposing a polycarbonate, which is capable of recovering a high-purity dihydroxy compound as a polycarbonate raw material at a high yield by decomposing a polycarbonate.

It is a further object of the present invention to provide an aqueous solution containing an aromatic dihydroxy compound in a high concentration stably.

Other objects and advantages of the present invention will become apparent from the following description.

According to the present invention, firstly, the above objects and advantages of the present invention are attained by a method of decomposing a polycarbonate, comprising decomposing the polycarbonate with water in a supercritical or subcritical state.

According to the present invention, secondly, the above objects and advantages of the present invention are attained by an aromatic dihydroxy compound aqueous solution which has a temperature of 10 to 100° C. and a pressure of 0.1 to 10 MPa and contains 1 wt % or more of an aromatic dihydroxy compound dissolved in water.

DETAILED DESCRIPTION OF THE PREFERRED EMBODIMENT

The polycarbonate to be decomposed by the present invention may be a polycarbonate itself or a polycarbonate contained in a thermoplastic composition comprising the polycarbonate and other thermoplastic resin.

The polycarbonate is any one of an aliphatic polycarbonate, alicyclic polycarbonate and aromatic polycarbonate. Out of these, it is preferably an aromatic polycarbonate, more preferably a polycarbonate comprising a recurring unit represented by the following formula (1):

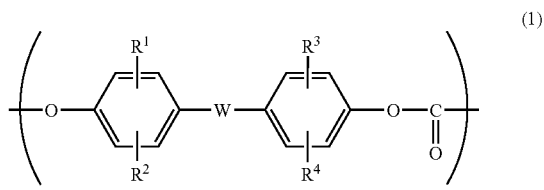

(1)

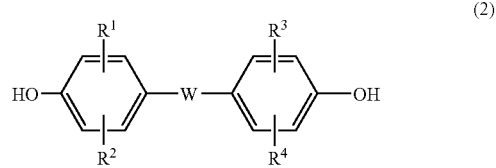

(2)

wherein $R^1$, $R^2$, $R^3$ and $R^4$ are each independently a hydrogen atom, alkyl group having 1 to 10 carbon atoms, cycloalkyl group having 6 to 10 carbon atoms, aryl group having 6 to 10 carbon atoms, aralkyl group having 7 to 10 carbon atoms or halogen atom, and W is a single bond, alkylene group having 1 to 10 carbon atoms, alkylidene group having 2 to 10 carbon atoms, cycloalkylene group having 6 to 10 carbon atoms, cycloalkylidene group having 6 to 10 carbon atoms, alkylene-arylene-alkylene group having 8 to 15 carbon atoms, oxygen atom, sulfur atom, sulfoxide group or sulfone group.

The alkyl group having 1 to 10 carbon atoms may be linear or branched. Examples of the alkyl group include methyl, ethyl, propyl, butyl, octyl and decyl. Examples of the aryl group having 6 to 10 carbon atoms include phenyl, tolyl, cumyl and naphthyl. Examples of the aralkyl group having 7 to 10 carbon atoms include benzyl, 2-phenethyl, 2-methyl and 2-phenylethyl.

$R^1$, $R^2$, $R^3$ and $R^4$ are preferably each independently a hydrogen atom, methyl group or t-butyl group, particularly preferably a hydrogen atom.

W is as defined hereinabove.

The alkylene group having 1 to 10 carbon atoms may be linear or branched. Examples of the alkylene group include methylene, 1,2-ethylene, 2,2-propylene, 2,2-butylene and 1,1-decylene.

Examples of the alkylidene group having 2 to 10 carbon atoms include ethylidene, propylidene, butylidene and hexylidene.

Examples of the cycloalkylene group having 6 to 10 carbon atoms include 1,4-cyclohexylene and 2-isopropyl-1,4-cyclohexylene.

Examples of the cycloalkylidene group having 6 to 10 carbon atoms include cyclohexylidene and isopropylcyclohexylidene.

Examples of the alkylene-arylene-alkylene group having 8 to 15 carbon atoms include m-diisopropylphenylene.

W is preferably a cyclohexylidene group or 2,2-propylidene group, particularly preferably 2,2-propylidene group.

The molecular weight of the polycarbonate used in the present invention is not particularly limited but its viscosity average molecular weight is preferably 10,000 to 250,000.

The polycarbonate is produced by a method known per se, for example, interfacial polycondensation between a dihydroxy compound and phosgene or melt polycondensation between a dihydroxy compound and a dialkyl carbonate.

The polycarbonate of the present invention can be an object of decomposition regardless of its production process.

In the present invention, a defective product and waste polymer which occurs in the course of production and a polycarbonate waste such as used CD can be used as an object of decomposition. In this case, the waste may contain impurities such as an al recording layer and may be decomposed directly or after impurities are removed.

Out of the above dihydroxy compounds, an aromatic dihydroxy compound which provides an aromatic polycarbonate is preferably represented by the following formula (2):

wherein $R^1$, $R^2$, $R^3$, $R^4$ and W are as defined in the above formula (1).

Examples of the aromatic dihydroxy compound include 2,2-bis(4-hydroxyphenyl)propane (namely, bisphenol A), bis(4-hydroxyphenyl)methane, 1,1-bis(4'-hydroxyphenyl)ethane, 1,2-bis(4'-hydroxyphenyl)ethane, bis(4-hydroxyphenyl)phenylmethane, 1,1-bis(4'-hydroxyphenyl)-1-phenylethane, 2-(4'-hydroxyphenyl)-2-(3'-hydroxyphenyl)propane, 2,2-bis(4'-hydroxyphenyl)butane, 1,1-bis(4'-hydroxyphenyl)isobutane and 4,4'-dihydroxydiphenyl. They may be used alone or in combination of two or more. Out of the above compounds, the aromatic polycarbonate which is particularly preferably used as an object of decomposition in the present invention is an aromatic polycarbonate obtained from 2,2-bis(4-hydroxyphenyl)propane.

The other thermoplastic resin which forms a thermoplastic composition with the above polycarbonate is not particularly limited but preferably an olefin-based resin.

Any olefin-based resin is acceptable if it forms a composition with the polycarbonate. Typical examples of the olefin-based resin include acrylonitrile-butadiene-styrene resin (commonly called "ABS resin"), polystyrene resin (PS resin), polymethyl methacrylate resin (PMMA resin) and polyethylene resin (PE resin). Out of these, ABS resin is widely used because it has impact resistance, heat and oil resistance and processability and its market is big. The above thermoplastic composition comprises preferably 10 to 95 wt %, more preferably 40 to 90 wt % of the polycarbonate and preferably 5 to 90 wt %, more preferably 10 to 60 wt % of the other thermoplastic resin.

The above ABS resin is a resin obtained by polymerizing a diene-based rubber with an aromatic vinyl-based monomer, vinyl cyanide-based monomer and optionally other vinyl-based monomer copolymerizable with these, i.e., a graft polymer obtained by polymerizing monomers in the presence of the above diene-based rubber, or a mixture of the graft polymer and a copolymer of monomers. The present invention can be applied to both of the graft polymer and the copolymer. The production process of the ABS resin is emulsion polymerization, suspension polymerization, bulk polymerization, solution polymerization or a combination thereof.

Examples of the above diene-based rubber include polybutadiene, styrene-butadiene copolymer and acrylonitrile-butadiene copolymer having a glass transition temperature of 0° C. or lower.

Examples of the above aromatic vinyl-based monomer include styrene, α-methylstyrene, o-methylstyrene, m-methylstyrene, p-methylstyrene, t-butylstyrene, α-methylvinyltoluene, dimethylstyrene, chlorostyrene, dichlorostyrene, bromostyrene, dibromostyrene and vinylnaphthalene. They may be used alone or in combination of two or more. Out of these, styrene is commonly used.

Examples of the above vinyl cyanide-based monomer include acrylonitrile, methacrylonitrile and fumaronitrile. They may be used alone or in combination of two or more. Out of these, acrylonitrile is commonly used.

Examples of the other monomer copolymerizable with the above aromatic vinyl-based monomer and vinyl cyanide-based monomer include unsaturated carboxylic acids and unsaturated dicarboxylic anhydrides such as acrylic acid, methacrylic acid, maleic acid, maleic anhydride and citraconic anhydride, unsaturated alkyl carboxylates such as methyl (meth)acrylate, ethyl (meth)acrylate, propyl (meth)acrylate and 2-ethylhexyl (meth)acrylate, and maleimide-based monomers such as maleimide, methylmaleimide, ethylmaleimide, N-phenylmaleimide and O-chloro-N-phenylmaleimide. They may be used alone or in combination of two or more.

The above thermoplastic resin composition may further contain additives such as a phosphorus-based flame retardant compound, halogen-based flame retardant compound, rubber-like material and fibrous/non-fibrous filler.

Examples of the phosphorus-based flame retardant compound include inorganic phosphorus compounds such as red phosphorus, phosphine, hypophosphorous acid, phosphorous acid, metaphosphoric acid, pyrophosphoric acid and phosphoric anhydride, and known organic phosphoric ester compounds.

Examples of the halogen-based flame retardant compound include tetrabromobisphenol A and derivatives thereof, tetrabromobisphenol S, polybromodiphenyl ether, brominated polycarbonate oligomers and modified products thereof, brominated epoxy oligomers and modified products thereof, brominated phenoxy resin, brominated polystyrene, brominated phenylene ether, tribromophenoxyethane, brominated triazine compounds and chlorinated condensation alicyclic compounds.

Examples of the rubber-like material include polymers having a glass transition temperature of −100° C. to 50° C., copolymers of the polymers, and isoprene-based, butadiene-based, olefin-based, polyester elastomer-based and acrylic polymers. They may be homopolymers or copolymers. Out of these, butadiene-based and olefin-based copolymers are generally used. The butadiene-based copolymers include styrene-butadiene block copolymer which is a copolymer with styrene and hydrogenated product thereof. Further, terpolymers comprising an acid component may also be used, as exemplified by acrylic acid-butadiene-styrene terpolymer and carboxylic acid/carboxylic anhydride-containing acid compound-butadiene-styrene terpolymer.

The fibrous filler is a filler having an aspect ratio of 2 to 100, depending on the target degree of reinforcement of the thermoplastic resin composition. Examples of the fibrous filler include glass fiber, carbon fiber, titanium oxide whisker and fibrous wollastonite.

The non-fibrous filler is widely used as it can improve strength and dimensional stability at the same time. It may be plate-like, particulate or amorphous. Examples of the non-fibrous filler include talc, mica, clay, silica, glass flake, glass bead and hollow filler. They may be used alone or in combination of two or more.

The above thermoplastic resin composition in the present invention may optionally contain an alicyclic saturated hydrocarbon resin, higher fatty acid ester, petroleum hydrocarbon, aromatic hydrocarbon-based petroleum resin, polyoxyalkylene, terpene, wax, fluororesin, antioxidant, release agent, antistatic agent, stabilizer, ultraviolet light absorber and pigment in addition to the above additives.

In the decomposition method of the present invention, the above polycarbonate or a polycarbonate contained in the above thermoplastic resin composition is decomposed with water in a supercritical or subcritical state. Water in a supercritical state may be referred to as "supercritical water" and water in a subcritical state may be referred to as "subcritical water" hereinafter. By the decomposition reaction of the present invention, the polycarbonate is decomposed into a corresponding dihydroxy compound and carbonic dioxide.

In general, a supercritical fluid refers to a substance at a temperature and a pressure higher than its critical temperature and its critical pressure. The supercritical water is water at a temperature higher than its critical temperature of 374° C. and a pressure higher than its critical pressure of 22 MPa. The subcritical water is water at a temperature of 350° C. or higher and a pressure of 18 MPa or higher and not in a supercritical state. It is known that the physical property values such as density, ion product, ion concentration and dielectric constant of the supercritical or subcritical water vary widely according to its temperature and pressure, and it is easy to control these. As a result, a reaction in the supercritical water or subcritical water may receive an acid/basic catalyst effect and a solvent effect which differ according to temperature and pressure. Further, since the supercritical water or subcritical water has lower viscosity than a liquid, the diffusion of a substance is fast, and a reaction in the supercritical water or subcritical water is less affected by the diffusion rate than a reaction in a liquid. From the viewpoint of practical use, it can be said that water is an ideal solvent because it is the most inexpensive, nontoxic and flame retardant, has a small load on environment and excellent heat stability and is rarely oxidized.

Decomposition in the present invention is carried out at preferably 374° C., which is the critical temperature of the supercritical water or subcritical water, to 500° C., more preferably 374 to 430° C. When the temperature is lower than 374° C., the decomposition rate of the polycarbonate greatly drops, thereby causing the production of the residual unreacted product disadvantageously. When the temperature is higher than 500° C., the thermal decomposition reaction of the obtained dihydroxy compound quickly proceeds, whereby a hydroxyl compound other than the dihydroxy compound of interest and a derivative thereof may be by-produced in large quantities and also the decomposition of the thermoplastic resin such as ABS resin may also proceed in the case of the thermoplastic resin composition, thereby producing various compounds, causing a reduction in the impurity of the product and complicating the recovery step.

Decomposition is carried out at a pressure of preferably 18 to 40 MPa, more preferably 20 to 30 MPa. When the pressure is higher than 40 MPa, great energy costs are required for the industrial process with the result of a great load on safety and economy. When the pressure is lower than 18 MPa, the above physical properties specific to the subcritical water are hardly obtained.

The present invention is preferably carried out at an ion product (Kw) of the supercritical water or subcritical water of $10^{-15}$ mol$^2$/kg$^2$ or less, more preferably $10^{-17}$ mol$^2$/kg$^2$ or less. Under the above condition, the polycarbonate or a polycarbonate contained in the resin composition can be decomposed in a very short period of time and a dihydroxy compound can be obtained at high selectivity. It is considered that this is because a reduction in the ion concentration of a reaction site provides the most suitable environment for the decomposition of the polycarbonate. When the ion product (Kw) is larger than $10^{-15}$ mol$^2$/kg$^2$, the decomposition rate of the polycarbonate drops disadvantageously. When the reaction time is extended under this condition, the decomposition reaction of a dihydroxy compound proceeds simultaneously with the decomposition of the polycarbonate, thereby reducing the purity and yield rate of the dihydroxy compound. In the present invention, the lower limit of the ion product is not particularly limited but preferably $10^{-23}$ mol$^2$/kg$^2$.

Further, the dielectric constant of the above supercritical water or subcritical water is preferably 10 or less, more preferably 5 or less. The dielectric constant is a coefficient indicative of the relationship between charge and force given thereby in a substance and an index of the polarity of a solvent. Since water has a very high dielectric constant of 80 at room temperature, it dissolves well an inorganic substance such as an electrolyte but rarely an organic substance. However, when the temperature is elevated, the dielectric constant of water gradually lowers and the dielectric constant of the supercritical water or subcritical water at 374° C. or higher is about 10 which is almost the same as that of an organic solvent having low polarity. As a result, an opposite phenomenon that an organic substance dissolves well but an inorganic substance rarely dissolves occurs unlike ordinary water. In the present invention, the permeability of the supercritical water or subcritical water into the polycarbonate or thermoplastic resin composition is improved by setting the dielectric constant to 10 or less, thereby making it possible to bring the supercritical water or subcritical water into contact with the polycarbonate efficiently. The dihydroxy compound which is a decomposed product is dissolved and dispersed into the supercritical water or subcritical water to suppress its secondary decomposition. When the dielectric constant is larger than the above value, the permeability of the supercritical water into the resin lowers and also the phase separation of the dihydroxy compound from the supercritical water or subcritical water occurs, whereby the decomposition of the dihydroxy compound proceeds at the interface between the separated phases.

The reaction time in the present invention is not particularly limited. Under the above conditions, the polycarbonate or a polycarbonate resin contained in the thermoplastic resin composition can be decomposed in a very short time, for example, less than 1 minute to 5 minutes. When the reaction time is extended, the decomposition of the obtained dihydroxy compound proceeds, thereby reducing the purity of the dihydroxy compound and throughput per unit time in the industrial process, or increasing the volume of the reactor disadvantageously.

The decomposition method of the present invention is preferably employed when the polycarbonate is an aromatic polycarbonate and an aromatic dihydroxy compound is formed as a decomposed product. When the aromatic polycarbonate comprises the recurring unit represented by the above formula (1), the decomposed product is an aromatic dihydroxy compound represented by the above formula (2).

When the dihydroxy compound formed by the above reaction is an aromatic dihydroxy compound, it is recovered as a semi-stable homogeneous aqueous solution dissolved in water and having a concentration of 1 wt % or more at a temperature of 10 to 100° C. and a pressure of 0.1 to 10 MPa. It is known that the solubility in water of the aromatic dihydroxy compound is about 100 ppm at a temperature of 25° C. and a pressure of 0.1 MPa. Under normal conditions, it rarely dissolves in water. Therefore, the above aqueous solution is obtained by decreasing the temperature and the pressure of the solution from the time when the aromatic dihydroxy compound dissolves in the supercritical water or subcritical water. It can be said that the above solution is an utterly new aqueous solution containing an aromatic dihydroxy compound in a higher concentration than the conventionally known aromatic dihydroxy compound aqueous solution. The acquisition of the decomposed product in the above state makes it possible to simplify industrial processes for purifying and recovering a product and also to prevent the blockage of a pipe or valve advantageously. In the present invention, the aromatic dihydroxy compound contained in the aqueous solution can be purified and recovered by known recrystallization to obtain a high-purity aromatic dihydroxy compound.

When the thermoplastic composition is an object of decomposition, the formed dihydroxy compound is obtained as a similar homogeneous aqueous solution as above.

Since a thermoplastic resin such as ABS resin has a low decomposition rate and remains as solid, a dihydroxy compound aqueous solution can be easily recovered by adding a solid-liquid separation step. When the thermoplastic resin composition contains an additive such as a filler, as the additive remains as solid, the solid-liquid separation step may be added. After separation, the aromatic dihydroxy compound contained in the aqueous solution can be purified and recovered by known recrystallization such as cooling and thereby a high-purity aromatic dihydroxy compound can be obtained. A thermoplastic resin such as ABS resin may be decomposed into oil according to treating conditions. In this case, it is possible to easily recover a dihydroxy compound from a water layer by liquid-liquid separation between the water layer and the oil layer in the industrial process.

The decomposition method of the present invention can be carried out by using a known polymer decomposition apparatus. This apparatus preferably comprises a reactor for carrying out hydrolysis with supercritical or subcritical water, supply means for supplying a polycarbonate or a thermoplastic resin composition and supercritical or subcritical water into this reactor, filtering means for filtering a treated fluid obtained after hydrolysis with the supercritical or subcritical water in the reactor with a filter to remove insoluble impurities, means of separating the filtered fluid into water and a dihydroxy compound which is a decomposed product, and water treating means for treating water separated by the separation means. The polycarbonate or thermoplastic resin composition which is a raw material to be recycled is supplied into the reactor after it is (1) crushed to be prepared as slurry, (2) molten by heating or (3) dissolved in a solvent, or (4) directly as solid. Impurities contained in the raw material to be recycled may be removed by rolling or the like in advance, by filtering means installed before the reactor in the above method (2) or (3), or by both. The reactor may be of a flow, semi-batch or batch type. When a reactor of a flow type is used, throughput can be increased advantageously. The reaction solvent and the raw material can be pre-heated with a heat-exchanger in the flow or semi-batch type system to be supplied into the reactor. The means of separating water from a dihydroxy compound is not particularly limited. According to the present invention, a high-purity dihydroxy compound can be crystallized only by cooling, and the crystallized dihydroxy compound can be separated by solid-liquid separation means such as a centrifugal separator. The separated water is treated with known water treating means to have predetermined quality so as to be recycled to the reactor where the treated water is re-used as make-up water for supercritical or subcritical water while high reaction controllability is ensured in the reactor, thereby making it possible to form an economical water cycle. Since high reaction controllability can be ensured in the reactor by supplying make-up water having predetermined quality, for example, water treated to have the same quality as pure water into the reactor as make-up water, the dihydroxy compound can be recovered at a high purity and a high yield.

The dihydroxy compound obtained by the present invention is purified as required and recycled to be polymerized with the above carbonate precursor, thereby making it possible to produce a high-quality and high-grade polycarbonate. Further, it can be used to produce a polycarbonate compound resin and other resin obtained from a dihydroxy compound. The above polymerization may be carried out by any known method but preferably interfacial polymerization or melt polymerization.

EXAMPLES

The following Examples are provided for the purpose of further illustrating the present invention but are in no way to be taken as limiting.

Example 1

0.11 g of a polycarbonate resin pellet (AD-5503 of Teijin Chemicals, Ltd.) was fed to a SUS316 tube type reactor having a total capacity of 6 ml, 1.1 g of water was fed to the reactor to ensure that the inside pressure of the reactor became 25 MPa, and the reactor was sealed up. After the inside of the reactor was substituted by argon to create an inert atmosphere, it was immersed in a sand bath preheated at 400° C. and kept for 3 minutes. Under the above conditions, the ion product Kw was $10^{-20}$ mol$^2$/kg$^2$ and the dielectric constant was 2. Thereafter, when the reactor was immersed in water to be cooled to room temperature and the content of the reactor was transferred to a glass bottle, the content was an achromatic transparent homogeneous aqueous solution at a temperature of 20° C. and a pressure of 0.1 MPa and no solid matter was observed. The generation of gas was observed when the content was taken out. Further, when the above aqueous solution was left to stand for a certain time, the precipitation of a needle-like crystal was seen.

Diethyl ether was added to the above aqueous solution containing the crystal and stirred. When an ether phase was analyzed by gas chromatography (HP5890), it was found that 0.1 g of 2,2-bis(4-hydroxyphenyl)propane (that is, bisphenol A) was contained. Therefore, the concentration of the 2,2-bis(4-hydroxyphenyl)propane aqueous solution right after recovery was calculated as about 10 wt % at 20° C. and 0.1 MPa. The recovery of the above 2,2-bis(4-hydroxyphenyl)propane was 99% of the theoretical yield. It was confirmed that the polycarbonate was completely decomposed by the above method and that only 2,2-bis(4-hydroxyphenyl)propane and carbon dioxide could be easily recovered.

Example 2

Decomposition was carried out in the same manner as in Example 1 except that 0.08 g of a polycarbonate resin pellet was fed to a reactor, 0.84 g of water was fed to the reactor to ensure that the inside pressure of the reactor became 25 MPa, and the reactor was immersed in a sand bath preheated at 420° C. The ion product and the dielectric constant under the above conditions are shown in Table 1. When the content was transferred to a glass bottle after the reaction, the content was an achromatic transparent homogeneous aqueous solution at a temperature of 20° C. and a pressure of 0.1 MPa, and no solid matter was observed at all. The amount of 2,2-bis(4-hydroxyphenyl)propane contained in the aqueous solution was obtained by the same method as in Example 1 and shown in Table 1.

Example 3

Decomposition was carried out in the same manner as in Example 1 except that 0.06 g of a polycarbonate resin pellet was fed to a reactor, 0.60 g of water was fed to the reactor to ensure that the inside pressure of the reactor became 20 MPa, and the reactor was immersed in a sand bath preheated at 400° C. The ion product and the dielectric constant under the above conditions are shown in Table 1. When the content was transferred to a glass bottle after the reaction, the content was an achromatic transparent homogeneous aqueous solution at a temperature of 20° C. and a pressure of 0.1 MPa, and no solid matter was observed at all. The amount of 2,2-bis(4-hydroxyphenyl)propane (bisphenol A) contained in the aqueous solution was obtained by the same method as in Example 1 and shown in Table 1.

Example 4

Decomposition was carried out in the same manner as in Example 1 except that 0.07 g of a polycarbonate resin pellet was fed to a reactor, 0.66 g of water was fed to the reactor to ensure that the inside pressure of the reactor became 25 MPa and the reactor was immersed in a sand bath preheated at 450° C. The ion product and the dielectric constant under the above conditions are shown in Table 1. The amount of 2,2-bis(4-hydroxyphenyl)propane (bisphenol A) contained in the aqueous solution obtained by decomposition was obtained and shown in Table 1.

Example 5

Decomposition was carried out in the same manner as in Example 1 except that 0.21 g of a polycarbonate resin pellet was fed to a reactor, 2.1 g of water was fed to the reactor to ensure that the inside pressure of the reactor became 30 MPa, and the reactor was immersed in a sand bath preheated at 400° C. The ion product and the dielectric constant under the above conditions are shown in Table 1. When the content was transferred to a glass bottle after the reaction, the content was an achromatic transparent homogeneous aqueous solution at a temperature of 20° C. and a pressure of 0.1 MPa, and no solid matter was observed at all. The amount of 2,2-bis(4-hydroxyphenyl)propane (bisphenol A) contained in the aqueous solution was obtained by the same method as in Example 1 and shown in Table 1.

Example 6

0.2 g of a polycarbonate/ABS resin pellet (of Teijin Chemicals, Ltd.) containing about 50 wt % of a polycarbonate was fed to a SUS316 tube type reactor having a total capacity of 6 ml, 1.1 g of water was fed to the reactor to ensure that the inside pressure of the reactor became 25 MPa, and the reactor was sealed up. After the inside of the reactor was substituted by argon to create an inert atmosphere, it was immersed in a sand bath preheated at 400° C. and kept for 4 minutes. Under the above conditions, the ion product Kw was $10^{-20}$ mol$^2$/kg$^2$ and the dielectric constant was 2. Thereafter, when the reactor was immersed in water to be cooled to room temperature and the content of the reactor was transferred to a glass bottle, the content was a transparent aqueous solution containing ABS resin solid. The generation of gas was observed when the content was taken out. Further, when the above aqueous solution was left to stand for a certain time, the precipitation of a needle-like crystal was seen.

The ABS resin solid was separated from the above aqueous solution containing the crystal by filtration, a cleaning fluid obtained by cleaning the filter and the ABS resin solid with diethyl ether was added to a water phase to carry out an extraction operation. When the ether phase was analyzed by gas chromatography (HP5890), it was found that 0.07 g of 2,2-bis(4-hydroxyphenyl)propane was contained. This was about 70% of the theoretical yield of 2,2-bis(4-hydroxyphenyl)propane obtained from the polycarbonate contained in the polycarbonate/ABS resin. Therefore, it was confirmed that the polycarbonate contained in the polycarbonate/ABS resin was decomposed by the above method and 2,2-bis(4-hydroxyphenyl)propane which is a useful chemical raw material could be easily and efficiently recovered.

Comparative Example 1

0.48 g of a polycarbonate resin pellet was fed to a reactor, 4.8 g of water was fed to the reactor to ensure that the inside pressure of the reactor became 30 MPa, and the reactor was immersed in a sand bath preheated at 270° C. and kept for 30 minutes. Under the above conditions, the ion product Kw was $10^{-11}$ mol$^2$/kg$^2$ and the dielectric constant was 25. Thereafter, when the reactor was immersed in water to be immediately cooled to room temperature and the content of the reactor was transferred to a glass bottle, the content contained 0.4 g of undecomposed polycarbonate, and the conversion of the polycarbonate was calculated as 16%.

When the content was analyzed by gas chromatography as in Example 1, it contained 0.01 g of 2,2-bis(4-hydroxyphenyl)propane. This is 3% of the theoretical yield. It was found that the decomposition reaction of the polycarbonate rarely proceeds under the above conditions and a large amount of a by-product is produced disadvantageously.

TABLE 1

| | | Treating conditions | | | | Bisphenol A | |
|---|---|---|---|---|---|---|---|
| | PC Amount (g) | Temperature (° C.) | Pressure (Mpa) | Ion product Kw (mol$^2$/kg$^2$) | Dielectric constant | Recovery amount (g) | Recovery percentage (%) |
| Ex. 1 | 0.11 | 400 | 25 | $10^{-20}$ | 2 | 0.10 | 99 |
| Ex. 2 | 0.08 | 420 | 25 | $10^{-21}$ | 2 | 0.07 | 97 |
| Ex. 3 | 0.06 | 400 | 20 | $10^{-22}$ | 2 | 0.05 | 91 |
| Ex. 4 | 0.07 | 450 | 25 | $10^{-22}$ | 2 | 0.04 | 72 |
| Ex. 5 | 0.21 | 400 | 30 | $10^{-15}$ | 6 | 0.10 | 54 |
| C. Ex. 1 | 0.48 | 270 | 30 | $10^{-11}$ | 25 | 0.01 | 3 |

Ex.: Example
C. Ex.: Comparative Example

The invention claimed is:

1. A polycarbonate decomposition method comprising decomposing an aromatic polycarbonate obtained from 2,2-bis(4-hydroxyphenyl)propane with water in a supercritical or subcritical state at an ion product (Kw) of $10^{-17}$ mol$^2$/kg$^2$ or less at a temperature of 374 to 430° C. and at a pressure of 18 to 30 MPa to form 2,2-bis(4-hydroxyphenyl)propane as a dihydroxy compound component of the aromatic polycarbonate.

2. The decomposition method according to claim 1, wherein the aromatic polycarbonate is contained in a thermoplastic composition containing the aromatic polycarbonate.

3. The decomposition method according to claim 1, wherein the aromatic dihydroxy compound is recovered by crystallization.

4. The decomposition method according to claim 1, wherein the dielectric constant of water in a supercritical or subcritical state is 10 or less.

* * * * *